(12) United States Patent
Samboju et al.

(10) Patent No.: US 8,653,327 B2
(45) Date of Patent: *Feb. 18, 2014

(54) LINEAR DNA MOLECULE DELIVERY USING PEGYLATED QUANTUM DOTS FOR STABLE TRANSFORMATION IN PLANTS

(75) Inventors: Narasimha C. Samboju, Carmel, IN (US); Kerrm Y. Yau, Carmel, IN (US); Frank Burroughs, Noblesville, IN (US); Jayakumar P. Samuel, Carmel, IN (US); Steven R. Webb, Westfield, IN (US)

(73) Assignee: Agrigenetics, Inc., Indianapolis, IN (US)

( * ) Notice: Subject to any disclaimer, the term of this patent is extended or adjusted under 35 U.S.C. 154(b) by 157 days.

This patent is subject to a terminal disclaimer.

(21) Appl. No.: 13/178,199

(22) Filed: Jul. 7, 2011

(65) Prior Publication Data

US 2012/0023619 A1     Jan. 26, 2012

Related U.S. Application Data

(60) Provisional application No. 61/362,224, filed on Jul. 7, 2010.

(51) Int. Cl.
| | | |
|---|---|---|
| C07K 14/415 | (2006.01) | |
| A01H 5/10 | (2006.01) | |
| A01H 1/04 | (2006.01) | |
| A01H 1/02 | (2006.01) | |
| B82Y 30/00 | (2011.01) | |
| B82Y 10/00 | (2011.01) | |
| B82Y 5/00 | (2011.01) | |
| C12N 15/87 | (2006.01) | |

(52) U.S. Cl.
USPC ........ 800/278; 800/293; 800/320.1; 800/265; 800/268; 977/704; 977/774; 977/808; 435/470; 435/430.1

(58) Field of Classification Search
None
See application file for complete search history.

(56) References Cited

U.S. PATENT DOCUMENTS

| | | | |
|---|---|---|---|
| 5,302,523 | A | 4/1994 | Coffee et al. |
| 5,464,765 | A | 11/1995 | Coffee et al. |
| 6,316,694 | B1 | 11/2001 | Dormann et al. |
| 2004/0181821 | A1 | 9/2004 | Zhou et al. |
| 2005/0123974 | A1 | 6/2005 | Gilmanshin et al. |
| 2006/0088903 | A1 | 4/2006 | Lang et al. |
| 2006/0223125 | A1 | 10/2006 | Lelkes et al. |
| 2009/0104700 | A1* | 4/2009 | Samuel et al. ............ 435/412 |

FOREIGN PATENT DOCUMENTS

WO     WO2008/045288     4/2008

OTHER PUBLICATIONS

Buhfeler, Egon et al., "Cascade- and nonskid-chain-like syntheses of molecular cavity topologies," Georg Thieme Publishers, 1978, pp. 155-158.

Haensler, Jean et al. "Polyamidoamine cacade polymers mediate efficient transfection of cells in culture," Bioconjugate Chem, 2005, pp. 372-379, vol. 4.
Pasupathy, Karthikeyan et al. "Direct plant gene delivery with a poly(amidoarnine) dendrimer." Biotechnology Journal, 2008, pp. 1078-1082, vol. 3.
Kihara, Fumihiro et al. "In vitro and in vivo gene transfer by optimized a-cyclodextrin conjugate with polyamido amine dendrimer," Bioconjugate Chem,, 2003, pp. 342-350, vol. 14.
Tang, Mary X., et al., "In vitro gene delivery by degraded polyamidoamine dendrimers," Bioconjugate Chem,1996, pp. 703-714, vol. 7.
Tomalia D.A., et al. "Dendrimers as multi-purpose nanodevices for oncology drug delivery and diagnostic imaging," Biochem. Soc. Trans. (2007) pp. 61-67.
Tomalia D.A. et al., "A new class of polymers: starburst-dendritic macromolecules," Polymer Journal, 1985, pp. 117-132, vol. 17, No. 1.
Agrawal, Pawan K. et al., "Transformation of plants with multiple cassettes generates simple transgene integration patterns and high expression levels," Moiec Breeding, (2005), pp. 247-260, vol. 16.
Fu, Xiangdong et al. "Linear transgene constructs lacking vector backbone sequences generate low-copy-number transgenic plants with simple integration patterns," Transgenic Res. (2000), pp. 11-19, vol. 9.
Kohli, Ajay et al., "Molecular characterization of transforming plasmid rearrangements in transgenic rice reveals recombination hot spot in the CaMV 35S promoter and confirms the predominance of microhomology mediated recombination," Plant J., 1999, pp. 591-601, vol. 17.
Kohli, Ajay et al., "Transgene organization in rice engineered through direct DNA transger supports a two-phase integration mechanism mediated by the establishment of integration hot spots," Proc. Natl. Aced, Sci USA Jun. 1998, pp. 7203-7208, vol. 95.
Loc, T.hi Nguyen et al.. "Linear transgene constructs lacking vector backbone sequences generate transgenic rice plants with accumulate higher levels of proteins conferring insect resistance" Molecular Breeding, (2002) , pp. 231-244, vol. 9.
Muller, A.E. et al. "Palindromic sequences and A+T-rich DNA elements promote illegitimate recombination in Nicotiana tabacum,", J. Mol. Biol.1999, pp. 29-46, vol. 291.
Nie, Shuming et al. "Probing single molecules and single nanoparticles by surface-enhanced raman scattering," Science, Feb. 21, 1997, pp. 1102-1106, vol. 275.
Pawloski, Wojciech P. et al., "Transgenic DNA integrated into the oat genome is frequently interspersed by host DNA," Proc. Natl. Acad. Sci USA, Oct. 1998, pp. 12106-12110, vol. 95.

(Continued)

Primary Examiner — David T Fox
Assistant Examiner — Jared Shapiro
(74) Attorney, Agent, or Firm — Ronald S. Maciak; TraskBritt, P.C.

(57) ABSTRACT

Methods for introducing a linear nucleic acid molecule of interest into a cell comprising a cell wall include use of nanoparticles coated with polyethylene glycol. In some embodiments, the cell comprising a cell wall is a plant cell. Methods include genetically or otherwise modifying plants and for treating or preventing disease in plant cells comprising a cell wall. Transgenic plants include a nucleic acid molecule of interest produced by regeneration of whole plants from plant cells transformed with linear nucleic acid molecules.

21 Claims, 3 Drawing Sheets

(56) References Cited

OTHER PUBLICATIONS

Romano, Andrea. et al. "Transgene organization in potato after paritlce bombardment-mediated (co-) transformation using plasmids and gene cassettes" Transgenic Res. (2003), pp. 461-473, vol. 12.

Svitashev, Sergei K. et al. "Complex transgene locus structures implicate multiple mechanisms for plant transgene rearrangement," Plant J. (2002), pp. 433-445, vol. 32.

Yezhelyev, Maksym V. et al. "Proton-sponge coated quantum dots for siRNA delivery and intracellular imaging," J. Am. Chem Soc., (2008), pp. 9006-9012, vol. 130.

International Search Report for International Application No. PCT/US2011/043221, dated Feb. 9, 2012.

Written Opinion or International Application No. PCT/US2011/043221, dated Feb. 9, 2012.

Muller, Frank et al., "Quantum dots—a versatile tool in plant sciences?" Journal of Nanobiotechnology, Jun. 15, 2006, pp. 1-5, vol. 4(5).

International Search Report for International Application No. PCT/US2011/043217, dated Feb. 9, 2012.

Written Opinion or International Application No. PCT/US2011/043217, dated Feb. 9, 2012.

von Groll et al., "Linear DNA Low Efficiency Transfection by Liposome can be Improved by the Use of Cationic Lipid as Charge Neutralizer" (2006), Biotechnol. Prog. 22:1220-1224.

Ziemienowicz et al., "A Novel Method of Transgene Delivery into Triticale Plants using the *Agrobacterium* T-DNA-Derived Nano-Complex" (2012), Plant Physiol., 158(4):1503-13.

\* cited by examiner

```
GCAGCCNGANATGGCCGCGGTTNGTGATATCGTTAACCATTACATTGAGACGCTCTACAG
|||||  ||  |||||||||||| |||||||||||||||||||||||||||| |||||||
GCAGC-TGATATGGCCGCGGTTTGTGATATCGTTAACCATTACATTGAGACG-TCTACAG

TGAACTTTAGGACAGAGCCACAAACACCACAAGAGTGGATTGATGATCTAGAGAGGTTGC
||||||||||||||||||||||||||||||||||||||||||||||||||||||||||||
TGAACTTTAGGACAGAGCCACAAACACCACAAGAGTGGATTGATGATCTAGAGAGGTTGC

AAGATAGATACCCTTGGTTGGTTGCTGAGGTTGAGGGTGTTGTGGCTGGTATTGCTTACG
||||||||||||||||||||||||||||||||||||||||||||||||||||||||||||
AAGATAGATACCCTTGGTTGGTTGCTGAGGTTGAGGGTGTTGTGGCTGGTATTGCTTACG

CTGGGCCCTGGAAGGCTAGGAACGCTTACGATTGGACAGTTGAGAGTACTGTTTACGTGT
||||||||||||||||||||||||||||||||||||||||||||||||||||||||||||
CTGGGCCCTGGAAGGCTAGGAACGCTTACGATTGGACAGTTGAGAGTACTGTTTACGTGT

CACATAGGCATCAAAGGTTGGGCCTAGGATCTACATTGTACACATTTGCTTAAGTCTA
|||||||||||||||||||||||||||||||  |||||||||||||||||||||||||
CACATAGGCATCAAAGGTTGGGCCTAGGATCCACATTGTACACATTTGCTTAAGTCTA

TGGAGGCGCAAGGTTTTAAGTCTGTGGTTGCTGTTATAGGCCTTCCAAACGATCCATCTG
||||||||||||||||||||||||||||||||||||||||||||||||||||||||||||
TGGAGGCGCAAGGTTTTAAGTCTGTGGTTGCTGTTATAGGCCTTCCAAACGATCCATCTG

TTAGGTTGCATGAGGCTTTGGGATACACAGCCCGGGGTACATTGCGCGCAGCTGGATACA
||||||||||||||||||||||||||||||||||||||||||||||||||||||||||||
TTAGGTTGCATGAGGCTTTGGGATACACAGCCCGGGGTACATTGCGCGCAGCTGGATACA

AGCATGGTGGATGGCATGATGTTGGTTTTTGGCAAAGGGATTTTGAGTTGCCAGCTCCTC
||||||||||||||||||||||||||||||||||||||||||||||||||||||||||||
AGCATGGTGGATGGCATGATGTTGGTTTTTGGCAAAGGGATTTTGAGTTGCCAGCTCCTC

CAAGGCCAGTTA
||||||||||||
CAAGGCCAGTTA
```

PAT original sequence from Gen bank (NCBI) is the top seqeunce

PAT from PCR product from Genomic DAN of Superfect mediated transgenic *Arabidopsis* is the bottom sequence

Fig. 3

```
SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Forward primer for YFP gene

<400> SEQUENCE: 1
tgttccacgg caagatcccc tacg                                             24

<210> SEQ ID NO 2
<211> LENGTH: 24
<212> TYPE: DNA
<213> ORGANISM: Artificial Sequence
<220> FEATURE:
<223> OTHER INFORMATION: Reverse primer for YFP gene

<400> SEQUENCE: 2
tattcatctg ggtgtgatcg gcca                                             24

<210> SEQ ID NO 3
<211> LENGTH: 24
<212> TYPE: DNA
<213> ORGANISM: Artificial Sequence
<220> FEATURE:
<223> OTHER INFORMATION: Forward primer for PAT gene

<400> SEQUENCE: 3
ggagaggaga ccagttgaga ttag                                             24

<210> SEQ ID NO 4
<211> LENGTH: 24
<212> TYPE: DNA
<213> ORGANISM: Artificial Sequence
<220> FEATURE:
<223> OTHER INFORMATION: Reverse primer for PAT gene

<400> SEQUENCE: 4
agatctgggt aactggccta actg                                             24
```

LINEAR DNA MOLECULE DELIVERY USING PEGYLATED QUANTUM DOTS FOR STABLE TRANSFORMATION IN PLANTS

CROSS-REFERENCE TO RELATED APPLICATION

This application claims the benefit of U.S. Provisional Patent Application Ser. No. 61/362,224, filed Jul. 7, 2010, the disclosure of which is hereby incorporated herein in its entirety by this reference.

FIELD OF THE DISCLOSURE

The present invention relates to methods using nanoparticles to non-invasively deliver linear nucleic acid molecules into plant cells having a cell wall.

BACKGROUND

Nanoparticles have unique properties that have been exploited to deliver DNA to specific animal cells. It has been found that when certain DNA-coated nanoparticles are incubated with cells not having a cell wall, the cells take up the nanoparticles and begin expressing genes encoded on the DNA. Semi-conductor nanoparticles (e.g., quantum dots ("QDs")) within the size range of 3-5 nm have also been used as carriers to deliver molecules into cells. DNA and proteins can be linked to certain ligands attached to the QD surface. See e.g., Patolsky, et al. (2003) J. Am. Chem. Soc. 125:13918. Carboxylic acid- or amine-coated QDs can be cross-linked to molecules containing a thiol group, see, e.g., Dubertret et al. (2002) Science 298:1759; Akerman, et al. (2002) Proc. Natl. Acad. Sci. U.S.A. 99:12617; Mitchell, et al. (1999) J. Am. Chem. Soc. 121:8122, or an N-hydroxysuccinimyl ("NHS") ester group, by using standard bioconjugation protocols. See, e.g., Pinaud, et al. (2004) J. Am. Chem. Soc. 126:6115; Bruchez, et al. (1998) Science 281:2013. An alternative way to attach molecules to the surface of QDs is via conjugation of streptavidin-coated QDs to biotinylated proteins, oligonucleotides, or antibodies. See, e.g., Dahan, et al. (2003) Science 302:442; Pinaud, et al. (2004) J. Am. Chem. Soc. 126:6115; Wu, et al. (2003) Nature Biotechnol. 21:41; Jaiswal, et al. (2003) Nature Biotechnol. 21:47; and Mansson, et al. (2004) Biochem. Biophys. Res. Commun. 314:529.

Delivery of foreign nucleic acid molecules to plants is challenging due to the presence of plant cell walls. Current methods rely on invasive delivery for genetic transformation of plants. In plant cells, the cell wall is a barrier against the delivery of exogenously applied molecules. Many invasive cell delivery methods, for example, biolisitic delivery (gene gun), microinjection, electroporation, and *Agrobacterium*-mediated transformation, have been employed to achieve gene and small molecule delivery into walled plant cells, but delivery of proteins has only been achieved by microinjection. Where nanoparticle delivery of nucleic acid molecules to plant cells is desired, the cell wall is removed before the addition of the particles to protoplasts of plant. See, for example, Torney, et al. (2007) Nature Nanotechnol. 2:295-300.

BRIEF SUMMARY OF THE DISCLOSURE

Described herein are methods and compositions for use of nanoparticles and linearized nucleic acid molecules for introducing a molecule of interest into a plant cell having a cell wall. Some embodiments of methods of the disclosure may be used to produce a stably-transformed genetically modified fertile plant. In some embodiments, the distinctive properties of linear nucleic acid molecules allow the delivery of specific gene sequences of interest without extraneous nucleic acid sequences that may have regulatory consequences for a transgenic target organism.

In some embodiments, nanoparticles may be PEGylated with linear nucleic acid molecules. In particular embodiments, the nanoparticles may be semi-conductor nanoparticles, such as quantum dots ("QDs"). In some embodiments, the linear nucleic acid molecules may be linearized plasmid DNA. In other embodiments, the linear nucleic acid molecules may comprise sequences encoding Phosphoinothricin-N-acetyltransferase (PAT) and/or Yellow fluorescence protein (YFP).

Also disclosed are methods for introducing a molecule of interest into a plant cell having a cell wall, wherein the methods may comprise providing the plant cell having a cell wall; coating the surface of nanoparticles with PEG to produce "PEGylated" nanoparticles; coating the PEGylated nanoparticles with at least one linear nucleic acid molecule of interest; placing the plant cell having a cell wall and the PEGylated nanoparticles coated with the linear nucleic acid molecule(s) of interest in contact with each other; and allowing uptake of the nanoparticle and the linear nucleic acid molecule(s) of interest into the cell comprising a cell wall.

Further disclosed are methods for introgressing a trait into a plant. In some embodiments, the method may comprise providing a plant cell; coating the surface of nanoparticles with PEG to produce PEGylated nanoparticles; coating the PEGylated nanoparticles with a means for expressing the trait in the plant; placing the plant cell and the PEGylated nanoparticles coated with means for expressing the trait in the plant in contact with each other; allowing uptake of the nanoparticle and the means for expressing the trait in the plant into the plant cell to produce a transformed plant cell; regenerating a whole plant from the transformed plant cell; and propagating the plant. In some embodiments, a trait that may be introgressed according to methods of the invention include a trait selected from, without limitation: male sterility; herbicide resistance; insect resistance; and resistance to bacterial disease, fungal disease, and/or viral disease.

Also disclosed are methods of the invention may be used for in planta transformation of a plant. In some embodiments, the plant may be selected from plants of the genus, *Arabidopsis*, for example, *A. thaliana*. In particular embodiments, a plant transformed by in planta transformation may be selected from *A. thaliana* plants of the Columbia ecotype.

Additionally disclosed are genetically modified (GM) plant cells and methods for generating them, wherein the plant cells have one or more nucleic acids introduced therein via methods of the present invention. In some embodiments, a plasmid comprising at least one gene of interest and a selectable marker may be in introduced into a plant cell having a cell well via a nanoparticle according to the present invention. In further embodiments, stable transformants may be selected that have stably integrated at least one gene of interest and/or the selectable marker. In alternative embodiments, a plant cell now comprising at least one gene of interest may be propagated to produce other cells comprising a molecule of interest. In other embodiments, plant cells now comprising a molecule of interest may be a regenerable cell that may be used to regenerate a whole plant including the molecule of interest.

Further disclosed are methods of creating regenerable plant cells comprising a molecule of interest for use in tissue culture. The tissue culture may be capable of regenerating plants having substantially the same genotype as the regenerable cells. The regenerable cells in such tissue cultures may be, for example, embryos; protoplasts; meristematic cells; callus; pollen; leaves; anthers; roots; root tips; flowers; seeds; pods; or stems. Still further, some embodiments provide plants regenerated from the tissue cultures of the invention.

Further disclosed are methods for generating stabilized plant lines comprising a desired trait or nucleic acid molecule of interest, wherein the desired trait or nucleic acid molecule of interest may be first introduced by uptake of a nanoparticle across a plant cell wall. Methods of generating stabilized plant lines are well known to one of ordinary skill in the art, and may include techniques such as, but not limited to, selfing; backcrossing; hybrid production; crosses to populations; and the like. Thus, also disclosed are plants and plant cells comprising a desired trait or nucleic acid molecule of interest first introduced into the plant cell (or its predecessors) by uptake of a nanoparticle across a cell wall. Plant cells comprising a desired trait or nucleic acid molecule of interest first introduced into the plant or cell (or its predecessors) by uptake of a nanoparticle across a cell wall can be used in crosses with other, different, plant cells to produce first generation ($F_1$) hybrid cells; seeds; and/or plants with desired characteristics.

In addition to the exemplary aspects and embodiments described above, further aspects and embodiments will become apparent in view of the following descriptions.

BRIEF DESCRIPTION OF THE FIGURES

FIG. 3 includes a sequence alignment between the Phosphoinothricin-N-acetyltransferase (PAT) DNA sequence from a nanoparticle with a linear DNA transformed *Arabidopsis* genome and the PAT sequence from the NCBI database.

SEQUENCE LISTING

Figure 1:
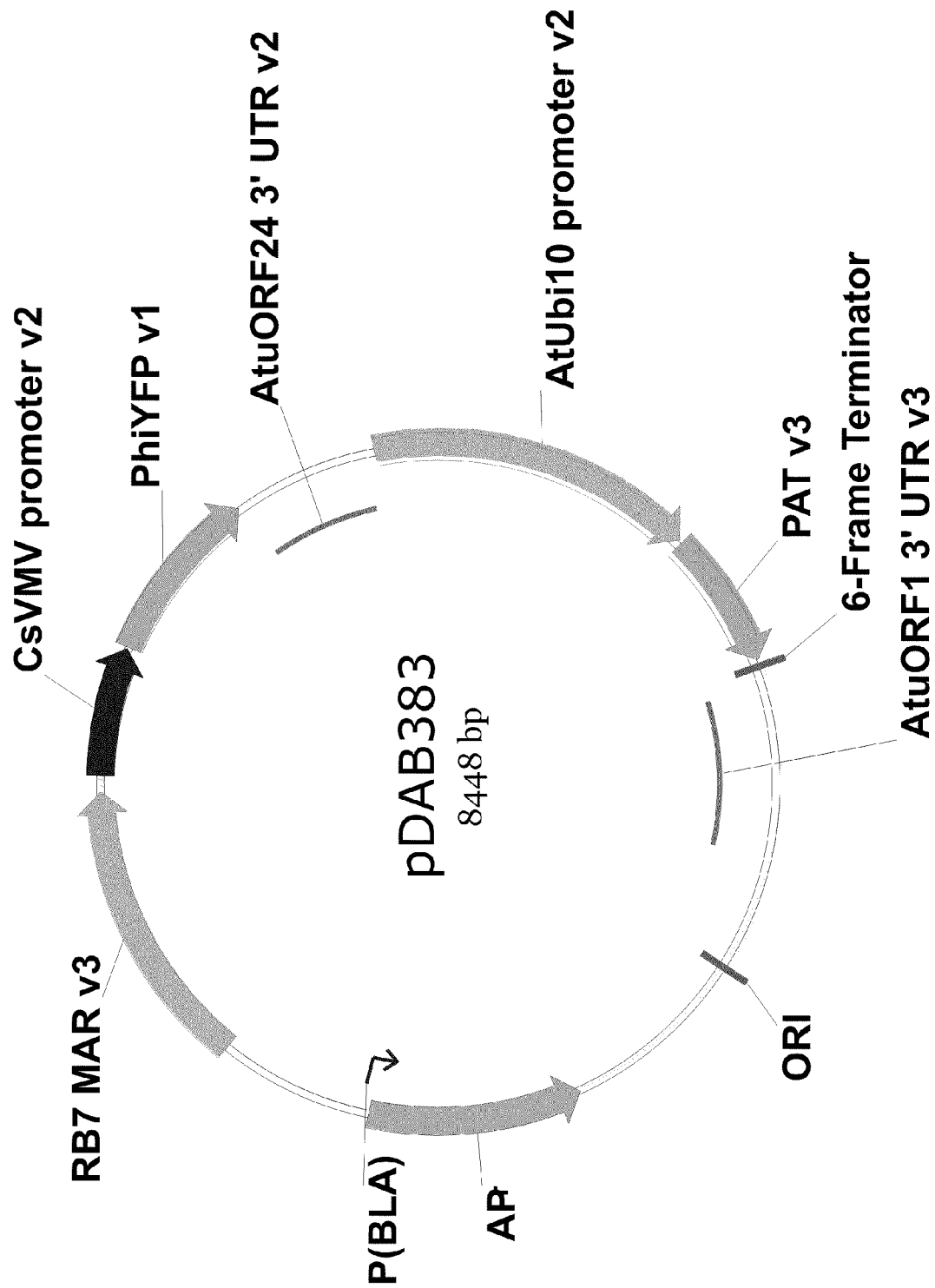
FIG. 1 includes a diagram of unlinearized plasmid pDAB3831.

SEQ ID NO:1 shows a forward primer sequence used to amplify the YFP gene:

TGTTCCACGGCAAGATCCCCTACG.

SEQ ID NO:2 shows a reverse primer sequence used to amplify the YFP gene:

TATTCATCTGGGTGTGATCGGCCA.

SEQ ID NO:3 shows a forward primer sequence used to amplify the PAT gene:

GGAGAGGAGACCAGTTGAGATTAG.

SEQ ID NO:4 shows a reverse primer sequence used to amplify the PAT gene:

AGATCTGGGTAACTGGCCTAACTG.

DETAILED DESCRIPTION

I. Overview of Several Embodiments

Methods of the invention allowing non-invasive gene transfer may be very useful for generating genetically-modified plants with desirable traits. Non-invasive gene transfer may facilitate the specific targeting and editing of molecular sites within the cells for areas, such as incorporating desirable input, output, and agronomic traits in crop plants. Described methods may also be useful as a non-GMO option for transient transformation of plants, expanding technology for trait introgression and disease resistance to tree or vegetable crops, wherein the technology is currently limited.

A recent patent application (U.S. Ser. No. 60/978,059) demonstrates a non-invasive means of DNA delivery based on nanoparticles using a variety of nanoparticle-pay-loads, inter alia, to deliver circular plasmid DNA, and unequivocally demonstrates the stable integration of transgenes in $T_1$ seeds of *Arabidopsis* plants. The transgenic plants containing the circular plasmid DNA produced therein displayed desired herbicide tolerance phenotypes and showed high levels of tolerance when sprayed with field levels of glufosinate ammonium at least 4 times concurrently. U.S. Ser. No. 60/978,059 demonstrated, inter alia, genetic transformation in *Arabidopsis* by positively charged gold nanoparticles using circular plasmid DNA. The present study describes, inter alia, the use of linear nucleic acid molecules for stable genetic transformation of plants.

U.S. Ser. No. 60/978,059 described, inter alia, positively charged nanoparticle-mediated plasmid DNA delivery. However, the demonstration of stable genomic integration of transgene using linear plasmid-based delivery has not been reported to date. This disclosure describes the use of positively charged nanoparticle-mediated linear nucleic acid molecules for stable genetic transformation in plants. Molecular analysis indicated the expression of PAT along with YFP in transgenic $T_1$ *Arabidopsis* plants transformed with a pat gene and a yfp gene by methods of the invention. The $T_1$ transgenic plants are fertile and produce seed. These seeds may be propagated, and a segregation analysis may be performed along with Molecular and protein analyses.

Linear nucleic acid molecules have distinctive properties which differentiate it from circular plasmid DNA. For example, linear nucleic acid molecules may have a well-defined gene cassette without the vector backbone and bacterial antibiotic selectable marker.

The herbicide, glufosinate ammonium (GLA), may be sprayed at a field level concentration for screening transgenics. *Arabidopsis* $T_1$ seedlings produced using methods of the invention have shown herbicide resistance against five applications of a field level dosage of glufosinate, for example, on alternate days beginning 7 days after germination. The genomic DNA from these transgenic plants were analyzed for the presence of pat and yfp by PCR, and the results have shown pat and yfp target DNA sequences. Sequencing of the PCR products results have revealed the correct sequences of pat and yfp transgenes in $T_1$ *Arabidopsis* produced using methods of the invention.

II. Terms

In the description and tables which follow, a number of terms are used. In order to provide a clear and consistent understanding of the specification and claims, including the scope to be given such terms, the following definitions are provided:

Backcrossing: As used herein the term, "backcrossing," may be a process in which a breeder repeatedly crosses hybrid progeny back to one of the parents, for example, a first generation hybrid $F_1$ with one of the parental genotypes of the $F_1$ hybrid.

Embryo: As used herein the term, "embryo," may refer to the small plant contained within a mature seed.

Nanoparticle: As used herein the term, "nanoparticle," may refer to a microscopic particle with at least one nanoscale dimension, for example, less than 100 nm. Nanoparticles suitable for use in the present invention may have a size of 1 nm-0.84 μm. One class of nanoparticles are "quantum dots" (QD). A quantum dot may have a median diameter of 1 nm-10 nm, for example, 2-4 nm. Other varieties of nanoparticle include, without limitation: gold nanoparticles; gold-coated nanoparticles; porous nanoparticles; mesoporous nanoparticles; silica nanoparticles; polymer nanoparticles, including dendrimers; tungsten nanoparticles; gelatin nanoparticles; nanoshells; nanocores; nanospheres; nanorods; magnetic nanoparticles; and combinations thereof.

Among available nanoparticles, luminescent semiconductor nanocrystals (QDs) provide many demonstrated applications in biological imaging and sensing. Their utility is derived from the combination of unique photo-physical characteristics and sizes comparable to that of a large protein. The hydrodynamic radius of hydrophilic CdSe—ZnS QDs varies from 5 nm (for nanocrystals cap exchanged with molecular ligands) to 20 nm for nanocrystals encapsulated within block copolymers. A single QD can be conjugated to several biomolecules (e.g., antibodies; peptides; and nucleic acid molecules) to provide multifunctional QD bioconjugates with enhanced avidity. In addition, their strong resistance to chemical and photo-degradation can potentially allow long-term fluorescent monitoring of specific biological processes. Nie and Emory (1997) Science 275:1102-6. Multiple non-covalent conjugation schemes based on metal affinity self-assembly and biotin-avidin binding can be simultaneously applied within the same complex, without requiring further purification, to produce multifunctional QD bioconjugates that are stable even in intracellular environments. Yezhelyev et al. (2008) J. Am. Chem. Soc. 130(28):9006-12. By utilizing an average of 10 YFPs plus a nominal 50 cell-penetrating peptides (CPPs) per QD, intracellular delivery of protein cargos with molecular weights of at least 300 kDa and a spatial extension of 150 angstroms can be achieved. Id. The delivered cargos for QD-b-PE conjugates have a much larger range of sizes and molecular weights; for instance, with an average of 2.5 Streptavidin-b-PE per conjugate, the delivered assemblies have a molecular weight that potentially exceeds $10^3$ kDa, and overall dimensions approaching 500 angstroms. Molecular weight and size can be increased substantially if conjugates with higher b-PE valencies are used.

Nucleic acid molecule: A polymeric form of nucleotides, which can include both sense and anti-sense strands of RNA, cDNA, genomic DNA, artificial chromosomes (ACEs), and synthetic forms and mixed polymers of the foregoing. A nucleotide refers to a ribonucleotide, deoxyribonucleotide, or a modified form of either type of nucleotide. A "nucleic acid molecule," as used herein, is synonymous with "nucleic acid" and "polynucleotide." A nucleic acid molecule is usually at least 10 bases in length, unless otherwise specified. The term includes single- and double-stranded forms of DNA. A nucleic acid molecule may include either or both naturally-occurring and modified nucleotides linked together by naturally-occurring and/or non-naturally occurring nucleotide linkages.

Operably linked: A first nucleic acid sequence is operably linked with a second nucleic acid sequence when the first nucleic acid sequence is in a functional relationship with the second nucleic acid sequence. For instance, a promoter is operably linked to a coding sequence if the promoter affects transcription or expression of the coding sequence. When recombinantly produced, operably linked nucleic acid sequences may be contiguous, and, where necessary to join two protein-coding regions, in the same reading frame. However, nucleic acids need not be contiguous to be operably-linked.

PEGylated: As used herein the term, "PEGylated," may refer to nanoparticles (e.g., quantum dots), wherein surfaces of the nanoparticles have been modified with polyethylene glycol (PEG) for improved biocompatibility. PEGylated nanoparticles may be further coated with various targeting ligands, for example, peptides and antibodies, for enhanced delivery efficiency to specific cells and tissues. PEG has been conjugated to nanoparticles with various drugs; liposomes; and polymeric micelles to, for example, prolong the blood circulation time of the coated nanoparticles by reducing the nonspecific adsorption of proteins via a steric stabilization effect.

Quantum dot: As used herein the term, "quantum dot," (QD) (also sometimes known as nanocrystals) may refer to a semiconductor nanostructure that confines the motion of conduction band electrons, valence band holes, or excitons (bound pairs of conduction band electrons and valence band holes) in all three spatial directions. The confinement may be due, for example, to electrostatic potentials (generated by external electrodes, doping, strain, impurities, etc.); the presence of an interface between different semiconductor materials (e.g., in core-shell nanocrystal systems); the presence of the semiconductor surface (e.g., semiconductor nanocrystal); or combinations thereof. A quantum dot may have a discrete quantized energy spectrum. The corresponding wave functions may be spatially localized within the quantum dot, but extend over many periods of the crystal lattice. A quantum dot contains a small finite number (for example, of the order of 1-100) of conduction band electrons; valence band holes; or excitons (i.e., a finite number of elementary electric charges).

Quantum dots are a special class of semiconducting materials, which may be crystals composed of periodic groups of II-VI, III-V, or IV-VI materials. Their sizes may range, for example, from 2-10 nanometers (10-50 atoms) in diameter. In some embodiments, quantum dots may be made of Cadmium Selenide Zinc Sulfide Core Shell (CdSe/ZnS), and have a range of useful electrical and optical properties that diverge in character from those of bulk material. Quantum dot nanoparticles have been investigated as an imaging agent in vivo and in vitro, because of their high quantum yield; high molar extinction coefficient; and high resistance to photobleaching.

Resistant to Glyphosate: Resistance to a dosage of glyphosate refers to the ability of a plant to survive (i.e. the plant may be not killed) by that dosage of glyphosate. In some cases, tolerant plants may temporarily yellow, or otherwise exhibit some glyphosate-induced injury (e.g., excessive tillering and/or growth inhibition), but recover.

Stabilized: As used herein the term, "stabilized," may refer to characteristics of a plant that are reproducibly passed from one generation to the next generation of inbred plants of the same variety.

Transgene: As used herein the term, "transgene," may refer to an exogenous nucleic acid sequence. In one example, a transgene is a gene sequence (e.g., a herbicide-resistance gene); a gene encoding an industrially or pharmaceutically useful compound; or a gene encoding a desirable agricultural trait. In yet another example, the transgene is an antisense nucleic acid sequence, wherein expression of the antisense nucleic acid sequence inhibits expression of a target nucleic acid sequence. A transgene may contain regulatory sequences operably linked to the transgene (e.g., a promoter). In some embodiments, a nucleic acid molecule of interest to be introduced by nanoparticle-mediated transformation is a transgene. However, in other embodiments, a nucleic acid molecule of interest is an endogenous nucleic acid sequence, wherein additional genomic copies of the endogenous nucleic acid sequence are desired; or a nucleic acid molecule that is in the antisense orientation with respect to a target nucleic acid molecule in the host organism.

Uptake: As used herein the term, "uptake," may refer to the translocation of a particle, such as a nanoparticle (for example, quantum dots), across a cell wall or a cellular membrane, wherein the translocation does not occur solely as a result of momentum imparted to the particle by something other than the cell into which the particle is being taken up. Non-limiting examples of devices or methods which cause translocation of a particle across a cell wall or a cell membrane solely as a result of momentum imparted to the particle are biolistic, gene gun, microinjection, and/or impalefection technologies.

III. DNA Molecule Delivery Using Nanoparticles for Stable Transformation of Plant Cells A. Overview This invention describes, for example, new methods for plant transformation using nanoparticle-mediated transfer of linearized plasmid DNA for genetic transformation and the development of stable transgenic plants. Methods according to certain embodiments may offer not only rapid generation of a transgenic organism, but also several possibilities for desired genomic modifications when compared to other transformation methods. Embodiments of the invention have led to the first reported stably-transformed plant produced via nanoparticle-mediated linearized plasmid DNA delivery. Disclosed methods of genetic modification are a departure from traditional methods of genetic transformation of plants, and may be very useful for generating transgenic crop plants.

B. DNA Molecules

With the advent of molecular biological techniques that have allowed the isolation and characterization of genes that encode specific protein or RNA products (e.g., interfering RNAs ("RNAi")), scientists in the field of plant biology developed a strong interest in engineering the genome of cells to contain and express foreign genes, or additional or modified versions of native or endogenous genes (perhaps driven by different promoters) in order to, for example, alter the traits of a cell in a specific manner. Such foreign additional and/or modified genes are referred to herein collectively as "transgenes." Transgenes may, for example, encode a protein of interest, or be transcribed into RNAi. Over the last fifteen to twenty years, several methods for producing transgenic cells have been developed and, in particular embodiments, the present invention relates to transformed versions of cells and methods of producing them via introducing into a plant cell having a cell wall one or more linear nucleic acid molecule(s) via uptake of a nanoparticle across a cell wall. In some embodiments of the invention, the transgene may be contained in a linearized expression vector.

Cell transformation may involve the construction of an expression vector which will function in a particular cell. Such a vector may comprise a nucleic acid sequence that includes a gene under control of, or operatively linked to, a regulatory element (for example, a promoter, an enhancer, a termination sequence, or combinations thereof). Thus, an expression vector may contain one or more such operably linked gene/regulatory element combinations. The vector(s) may be in the form of a plasmid and may be used alone or in combination with other plasmids to provide transformed cells using transformation methods as described herein to incorporate transgene(s) into the genetic material of a plant cell comprising a cell wall.

In embodiments, a nucleic acid molecule of interest may be a linear nucleic acid molecule. Linear nucleic acid molecules may be generated, for example, by digestion of a circular plasmid with a restriction endonuclease. Restriction endonucleases will cleave a plasmid at one or more recognition sites within the plasmid nucleotide sequence. Thus, plasmids may be designed to allow for the generation of one or more specific linear nucleic acid molecules by digestion with a particular restriction endonuclease. Alternatively, a given plasmid nucleotide sequence may be searched for recognition sites of one or more particular restriction endonuclease(s) that allow for generation of one or more specific linear nucleic acid molecule(s). By selecting restriction sites that cleave at specific locations within a circular plasmid or linear nucleic acid molecule, resulting linear nucleic acid molecules may be generated that lack one or more sequences from the precursor nucleic acid molecule. For example, a linear nucleic acid molecule may be generated that lacks extraneous nucleic acid sequences (e.g., vector backbone; selection markers, such as bacterial selection markers; and unnecessary nucleic acid sequences that are homologous to genomic DNA of the target cell). Alternatively, a linear nucleic acid molecule may be synthesized that lacks extraneous nucleic acid sequences.

In embodiments wherein the molecule of interest comprises one or more gene(s), the gene(s) may be a dominant or recessive allele. By way of example, the gene(s) may confer such traits as herbicide resistance, insect resistance, resistance for bacterial resistance, fungal resistance, viral disease resistance, male fertility, male sterility, enhanced nutritional quality, and industrial usage. Genes conferring these traits and other traits are known in the art, and any gene may be introduced into a cell comprising a cell wall according to methods of the invention.

Expression Vectors for Linearization and Uptake Via Nanoparticles: Marker Genes

Expression vectors may optionally include at least one genetic marker, for example, operably linked to a regulatory element that allows transformed cells containing the marker to be either recovered by negative selection (i.e., inhibiting growth of cells that do not contain the selectable marker gene) or by positive selection (i.e., screening for the product encoded by the genetic marker). Many selectable marker genes for transformation are well known in the art, and include for example and without limitation: genes that code for enzymes that metabolically detoxify a selective chemical agent which may be an antibiotic or an herbicide; or genes that encode an altered target which may be insensitive to the inhibitor. Specific positive selection methods are also known in the art.

One selectable marker gene which may be suitable for plant transformation with certain nucleic acid molecules is the neomycin phosphotransferase II (nptII) gene, optionally under the control of plant regulatory signals, which confers resistance to kanamycin. See, e.g., Fraley et al. (1983) Proc. Natl. Acad. Sci. U.S.A. 80:4803. Another selectable marker gene which may be used is the hygromycin phosphotransferase gene, which confers resistance to the antibiotic hygromycin. See, e.g., Vanden Elzen et al. (1985) Plant Mol. Biol. 5:299.

Additional selectable marker genes which may be used in methods of the invention include those of bacterial origin, for example, those that confer resistance to antibiotics such as gentamycin acetyl transferase, streptomycin phosphotransferase, aminoglycoside-3'-adenyl transferase, and bleomycin. See Hayford et al. (1988) Plant Physiol. 86:1216; Jones et al. (1987) Mol. Gen. Genet. 210:86; Svab et al. (1990) Plant Mol. Biol. 14:197; and Hille et al. (1986) Plant Mol. Biol. 7:171. Other selectable marker genes may confer resistance to herbicides such as glyphosate; glufosinate; or bromoxynil. See Comai et al. (1985) Nature 317:741-744; Gordon-Kamm et al. (1990) Plant Cell 2:603-618; and Stalker et al. (1988) Science 242:419-423.

Other selectable marker genes which may be used in methods of the invention include those that are not of bacterial origin. These genes include, for example and without limitation, mouse dihydrofolate reductase; plant 5-enolpyruvylshikimate-3-phosphate synthase; and plant acetolactate synthase. See Eichholtz et al. (1987) Somatic Cell Mol. Genet. 13:67; Shah et al. (1986) Science 233:478; and Charest et al. (1990) Plant Cell Rep. 8:643.

Another class of marker genes suitable for plant transformation may require screening of presumptively transformed plant cells rather than direct genetic selection of transformed cells for resistance to a toxic substance, such as an antibiotic. These genes are particularly useful to quantify or visualize the spatial pattern of expression of a gene in specific tissues, and are frequently referred to as "reporter genes," because they can be fused to a gene or gene regulatory sequence for the investigation of gene expression. Commonly used genes for screening transformed cells include, without limitation, β-glucuronidase (GUS); β-galactosidase; luciferase; and chloramphenicol acetyltransferase. See Jefferson (1987) Plant Mol. Biol. Rep. 5:387; Teeri et al. (1989) EMBO J. 8:343; Koncz et al. (1987) Proc. Natl. Acad. Sci. U.S.A. 84:131; and DeBlock et al. (1984) EMBO J. 3:1681. Recently, in vivo methods for visualizing GUS activity that do not require destruction of plant tissue have been made available. Molecular Probes publication 2908 (1993) IMA-GENE GREEN™, pp. 1-4; and Naleway et al. (1991) J. Cell Biol. 115:151a.

More recently, genes encoding Fluorescent Proteins (e.g., GFP, EGFP, EBFP, ECFP, and YFP) have been utilized as markers for gene expression in prokaryotic and eukaryotic cells. See Chalfie et al. (1994) Science 263:802. Thus, fluorescent proteins and mutations of fluorescent proteins may be used as screenable markers in some embodiments.

Expression Vectors for Uptake Via Nanoparticle: Promoters

Genes included in expression vectors may be driven by a nucleotide sequence comprising a regulatory element, for example, a promoter. Several types of promoters are now well known in the transformation arts, as are other regulatory elements that can be used alone or in combination with promoters.

A promoter is be a region of DNA that may be upstream from the start of transcription, and may be involved in recognition and binding of RNA polymerase and/or other proteins to initiate transcription. A "plant promoter" may be a promoter capable of initiating transcription in plant cells. Examples of promoters under developmental control include promoters that preferentially initiate transcription in certain tissues, such as leaves; roots; seeds; fibers; xylem vessels; tracheids; or sclerenchyma. Such promoters are referred to as "tissue-preferred." Promoters which initiate transcription only in certain tissues are referred to as "tissue-specific." A "cell type" specific promoter primarily drives expression in certain cell types in one or more organs, for example, vascular cells in roots or leaves. An "inducible" promoter may be a promoter which may be under environmental control. Examples of environmental conditions that may affect transcription by inducible promoters include, without limitation, anaerobic conditions or the presence of light. Tissue-specific, tissue-preferred, cell type specific, and inducible promoters constitute the class of "non-constitutive" promoters. A "constitutive" promoter is a promoter which may be active under most environmental conditions.

1. Inducible Promoters

An inducible promoter may be operably linked to a gene for expression in a cell. Optionally, the inducible promoter may be operably linked to a nucleotide sequence encoding a signal sequence which may be operably linked to a gene for expression in a cell. With an inducible promoter, the rate of transcription increases in response to an inducing agent.

Any inducible promoter can be used in embodiments of the instant invention. See Ward et al. (1993) Plant Mol. Biol. 22:361-366. Exemplary inducible promoters include without limitation: those from the ACEI system that responds to copper (Mett et al. (1993) Proc. Natl. Acad. Sci. U.S.A. 90:4567-71); an In2 gene from maize that responds to benzenesulfonamide herbicide safeners (Hershey et al. (1991) Mol. Gen. Genetics 227:229-237; and Gatz et al. (1994) Mol. Gen. Genetics 243:32-38); and Tet repressor from Tn10 (Gatz et al. (1991) Mol. Gen. Genetics 227:229-237). A particularly useful inducible promoter may be a promoter that responds to an inducing agent to which plants do not normally respond. Such an exemplary inducible promoter is the inducible promoter from a steroid hormone gene, the transcriptional activity of which may be induced by a glucocorticosteroid hormone. Schena et al. (1991) Proc. Natl. Acad. Sci. U.S.A. 88:0421.

2. Constitutive Promoters

A constitutive promoter may be operably linked to a gene for expression in a cell, or the constitutive promoter may be operably linked to a nucleotide sequence encoding a signal sequence which may be operably linked to a gene for expression in a cell.

Different constitutive promoters may be utilized in embodiments of the instant invention. Exemplary constitutive promoters include without limitation: promoters from plant viruses, such as the 35S promoter from CaMV (Odell et al. (1985) Nature 313:810-812); promoters from rice actin genes (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); maize H3 histone (Lepetit et al. (1992) Mol. Gen. Genetics 231:276-285 and Atanassova et al. (1992) Plant Journal 2 (3): 291-300); and the ALS promoter, XbaI/NcoI fragment 5' to the *Brassica napus* ALS3 structural gene (or a nucleotide sequence similarity to said XbaI/NcoI fragment). See International PCT Publication WO 96/30530.

3. Tissue-Specific or Tissue-Preferred Promoters

A tissue-specific promoter may be operably linked to a gene for expression in a cell. Optionally, the tissue-specific promoter may be operably linked to a nucleotide sequence encoding a signal sequence which may be operably linked to a gene for expression in a cell. Plants transformed with a gene of interest operably linked to a tissue-specific promoter may produce the protein product of the transgene exclusively, or preferentially, in a specific tissue.

Any tissue-specific or tissue-preferred promoter may be utilized in embodiments of the instant invention. Exemplary tissue-specific or tissue-preferred promoters include without limitation: a root-preferred promoter, for example, a promoter from the phaseolin gene (Murai et al. (1983) Science 23:476-82 and Sengupta-Gopalan et al. (1985) Proc. Natl. Acad. Sci. U.S.A. 82:3320-4); a leaf-specific and light-induced promoter, for example, a promoter from cab or rubisco (Simpson et al. (1985) EMBO J. 4(11):2723-2729 and Timko et al. (1985) Nature 318:579-82); an anther-specific promoter, for example, a promoter from LAT52 (Twell et al. (1989) Mol. Gen. Genetics 217:240-5); a pollen-specific promoter, for example, a promoter from Zm13 (Guerrero et al. (1993) Mol. Gen. Genetics 244:161-8); and a microspore-preferred promoter, for example, a promoter from apg (Twell et al. (1993) Sex. Plant Reprod. 6:217-24).

Transport of protein produced by transgenes to a subcellular compartment, such as the chloroplast; vacuole; peroxisome; glyoxysome; cell wall; or mitochondrion, or for secretion into the apoplast, may be accomplished by means of operably linking the nucleotide sequence encoding a signal sequence to the 5' and/or 3' region of a gene encoding the protein of interest. Targeting sequences at the 5' and/or 3' end of the gene may determine, for example, during protein synthesis and processing, where the encoded protein may be ultimately compartmentalized. Alternatively, such subcellular compartment targeting proteins may be directly linked to a nanoparticle to direct the nanoparticle coated with the nucleic acid molecule of interest to the desired subcellular compartment.

The presence of a signal sequence may direct a polypeptide to either an intracellular organelle or subcellular compartment, or for secretion to the apoplast. Many signal sequences are known in the art. See, e.g., Becker et al. (1992) Plant Mol. Biol. 20:49; Close, P. S., Master's Thesis, Iowa State University (1993), Knox et al. (1987) Plant Mol. Biol. 9:3-17; Lerner et al. (1989) Plant Physiol. 91:124-9; Fontes et al. (1991) Plant Cell 3:483-96; Matsuoka et al. (1991) Proc. Natl. Acad. Sci. U.S.A. 88:834; Gould et al. (1989) J. Cell. Biol. 108: 1657; Creissen et al. (1991) Plant J. 2:129; Kalderon et al. (1984) Cell 39:499-509; Steifel et al. (1990) Plant Cell 2:785-93.

Foreign Protein Genes and Agronomic Genes

Transgenic plants according to embodiments of the present invention may produce a foreign protein in commercial quantities. Thus, techniques for the selection and propagation of transformed plants yield a plurality of transgenic plants which are harvested in a conventional manner. A foreign protein then may be extracted from a tissue of interest, or from total biomass. Protein extraction from plant biomass can be accomplished by known methods which are discussed, for example, in Heney and On (1981) Anal. Biochem. 114:92-6.

In some aspects of the invention, plant material provided for commercial production of foreign protein may be a plant, plant tissue, or plant cell. In some aspects, the biomass of interest may be plant seed. For the transgenic plants that show higher levels of expression, a genetic map can be generated, for example, via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location may be useful, for example, for proprietary protection of a subject transgenic plant, or for biosafety evaluation. If unauthorized propagation may be undertaken and crosses made with other germplasm, the map of the integration region can be compared to similar maps for suspect plants to determine if the latter have a common parentage with the subject plant. Map comparisons may involve hybridizations, RFLP, PCR, SSR and sequencing, all of which are conventional techniques.

Likewise, agronomic genes may be expressed in transformed cells or their progeny. More particularly, plants can be genetically engineered via methods of the invention to express various phenotypes of agronomic interest. Exemplary genes that may be used in this regard include, but are not limited to, those categorized below.

1. Genes that Confer Resistance to Pests or Disease:

A) Plant disease resistance genes. Plant defenses are often activated by specific interaction between the product of a disease resistance gene (R) in the plant and the product of a corresponding avirulence (Avr) gene in the pathogen. A plant variety may be transformed with cloned resistance genes to engineer plants that are resistant to specific pathogen strains. See, e.g., Jones et al. (1994) Science 266:789 (cloning of the tomato Cf-9 gene for resistance to *Cladosporium fulvum*); Martin et al. (1993) Science 262:1432 (tomato Pto gene for resistance to *Pseudomonas syringae* pv. tomato encodes a protein kinase); Mindrinos et al. (1994) Cell 78:1089 (RSP2 gene for resistance to *Pseudomonas syringae*).

B) A gene conferring resistance to a pest, for example, soybean cyst nematode. See, e.g., International PCT Publication WO 96/30517; and International PCT Publication WO 93/19181.

C) A *Bacillus thuringiensis* protein, a derivative thereof, or a synthetic polypeptide modeled thereon. See, e.g., Geiser et al. (1986) Gene 48:109 (cloning and nucleotide sequence of a Bt δ-endotoxin gene). Moreover, DNA molecules encoding δ-endotoxin genes can be purchased from American Type Culture Collection (Manassas, Va.), for example, under ATCC Accession Nos. 40098; 67136; 31995; and 31998.

D) A lectin. See, for example, Van Damme et al. (1994) Plant Molec. Biol. 24:25 (nucleotide sequences of several *Clivia miniata* mannose-binding lectin genes).

E) A vitamin-binding protein, for example, avidin. See International PCT Publication US93/06487 (use of avidin and avidin homologues as larvicides against insect pests).

F) An enzyme inhibitor, for example, a protease or proteinase inhibitor, or an amylase inhibitor. See, e.g., Abe et al. (1987) J. Biol. Chem. 262:16793 (nucleotide sequence of rice cysteine proteinase inhibitor); Huub et al. (1993) Plant Molec. Biol. 21:985 (nucleotide sequence of cDNA encoding tobacco proteinase inhibitor I); Sumitani et al. (1993) Biosci. Biotech. Biochem. 57:1243 (nucleotide sequence of *Streptomyces nitrosporeus* alpha-amylase inhibitor) and U.S. Pat. No. 5,494,813.

G) An insect-specific hormone or pheromone, for example, an ecdysteroid or juvenile hormone, a variant thereof, a mimetic based thereon, or an antagonist or agonist thereof. See, e.g., Hammock et al. (1990) Nature 344:458 (baculovirus expression of cloned juvenile hormone esterase, an inactivator of juvenile hormone).

H) An insect-specific peptide or neuropeptide which, upon expression, disrupts the physiology of the affected pest. See, e.g., Regan (1994) J. Biol. Chem. 269:9 (expression cloning yields DNA coding for insect diuretic hormone receptor); and Pratt et al. (1989) Biochem. Biophys. Res. Comm. 163:1243 (an allostatin may be identified in *Diploptera puntata*). See also U.S. Pat. No. 5,266,317 (genes encoding insect-specific, paralytic neurotoxins).

I) An insect-specific venom produced in nature by a snake, a wasp, or any other organism. See, e.g., Pang et al. (1992)

Gene 116:165 (heterologous expression in plants of a gene coding for a scorpion insectotoxic peptide).

J) An enzyme responsible for a hyperaccumulation of a monoterpene, a sesquiterpene, a steroid, hydroxamic acid, a phenylpropanoid derivative or another non-protein molecule with insecticidal activity.

K) An enzyme involved in the modification, including the post-translational modification, of a biologically active molecule, for example, a glycolytic enzyme; a proteolytic enzyme; a lipolytic enzyme; a nuclease; a cyclase; a transaminase; an esterase; a hydrolase; a phosphatase; a kinase; a phosphorylase; a polymerase; an elastase; a chitinase; or a glucanase, whether natural or synthetic. See International PCT Publication WO 93/02197 (nucleotide sequence of a callase gene). DNA molecules which contain chitinase-encoding sequences can be obtained, for example, from the ATCC, under Accession Nos. 39637 and 67152. See also Kramer et al. (1993) Insect Biochem. Molec. Biol. 23:691 (nucleotide sequence of a cDNA encoding tobacco hornworm chitinase); and Kawalleck et al. (1993) Plant Molec. Biol. 21:673 (nucleotide sequence of the parsley ubi4-2 polyubiquitin gene).

L) A molecule that stimulates signal transduction. See, e.g., Botella et al. (1994) Plant Molec. Biol. 24:757 (nucleotide sequences for mung bean calmodulin cDNA clones); and Griess et al. (1994) Plant Physiol. 104:1467 (nucleotide sequence of a maize calmodulin cDNA clone).

M) A hydrophobic moment peptide. See, e.g., International PCT Publication WO 95/16776 (peptide derivatives of Tachyplesin which inhibit fungal plant pathogens); and International PCT Publication WO 95/18855 (synthetic antimicrobial peptides that confer disease resistance).

N) A membrane permease, a channel former, or a channel blocker. See, e.g., Jaynes et al. (1993) Plant Sci 89:43 (heterologous expression of a cecropin-β lytic peptide analog to render transgenic tobacco plants resistant to *Pseudomonas solanacearum*).

O) A viral-invasive protein or a complex toxin derived therefrom. For example, the accumulation of viral coat proteins in transformed plant cells imparts resistance to viral infection and/or disease development effected by the virus from which the coat protein gene may be derived, as well as by related viruses. See Beachy et al. (1990) Ann. rev. Phytopathol. 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P) An insect-specific antibody or an immunotoxin derived therefrom. Thus, an antibody targeted to a critical metabolic function in the insect gut may inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q) A virus-specific antibody. See, e.g., Tavladoraki et al. (1993) Nature 366:469 (transgenic plants expressing recombinant antibody genes are protected from virus attack).

R) A developmental-arrestive protein produced in nature by a pathogen or a parasite. For example, fungal endo α-1,4-D-polygalacturonases facilitate fungal colonization and plant nutrient release by solubilizing plant cell wall homo-α-1,4-D-galacturonase. See Lamb et al. (1992) Bio/Technology 10:1436. See also Toubart et al. (1992) Plant J. 2:367 (cloning and characterization of a gene which encodes a bean endopolygalacturonase-inhibiting protein).

S) A developmental-arrestive protein produced in nature by a plant. See, e.g., Logemann et al. (1992) Bio/Technology 10:305 (transgenic plants expressing the barley ribosome-inactivating gene have an increased resistance to fungal disease).

2. Genes that Confer Resistance to an Herbicide:

A) An herbicide that inhibits the growing point or meristem, for example, an imidazolinone or a sulfonylurea. Exemplary genes in this category code for mutant ALS and AHAS enzyme as described, for example, by Lee et al. (1988) EMBO J. 7:1241, and Miki et al. (1990) Theor. Appl. Genet. 80:449, respectively.

B) Glyphosate resistance conferred by, for example, mutant 5-enolpyruvylshikimate-3-phosphate synthase (EPSPs) genes (via the introduction of recombinant nucleic acids and/or various forms of in vivo mutagenesis of native EPSPs genes); aroA genes and glyphosate acetyl transferase (GAT) genes, respectively); other phosphono compounds such as glufosinate phosphinothricin acetyl transferase (PAT) genes from *Streptomyces* species, including *Streptomyces hygroscopicus* and *Streptomyces viridichromogenes*); and pyridinoxy or phenoxy proprionic acids and cyclohexones (ACCase inhibitor-encoding genes). See, e.g., U.S. Pat. No. 4,940,835; and U.S. Pat. No. 6,248,876 (nucleotide sequences of forms of EPSPs which can confer glyphosate resistance to a plant). A DNA molecule encoding a mutant aroA gene can be obtained under ATCC accession number 39256. See also U.S. Pat. No. 4,769,061 (nucleotide sequence of a mutant aroA gene). European patent application No. 0 333 033 and U.S. Pat. No. 4,975,374 disclose nucleotide sequences of glutamine synthetase genes, which may confer resistance to herbicides such as L-phosphinothricin. Nucleotide sequences of exemplary PAT genes are provided in European application No. 0 242 246, and DeGreef et al. (1989) Bio/Technology 7:61 (production of transgenic plants that express chimeric bar genes coding for PAT activity). Exemplary of genes conferring resistance to phenoxy proprionic acids and cyclohexones, such as sethoxydim and haloxyfop, include the Acc1-S1, Acc1-S2 and Acc1-S3 genes described by Marshall et al. (1992) Theor. Appl. Genet. 83:435. GAT genes capable of conferring glyphosate resistance are described, for example, in WO 2005012515. Genes conferring resistance to 2,4-D, fop and pyridyloxy auxin herbicides are described, for example, in WO 2005107437.

C) An herbicide that inhibits photosynthesis, such as a triazine (psbA and gs+ genes) or a benzonitrile (nitrilase gene). See, e.g., Przibila et al. (1991) Plant Cell 3:169 (transformation of *Chlamydomonas* with plasmids encoding mutant psbA genes). Nucleotide sequences for nitrilase genes are disclosed in U.S. Pat. No. 4,810,648, and DNA molecules containing these genes are available under ATCC Accession Nos. 53435; 67441; and 67442. See also Hayes et al. (1992) Biochem. J. 285:173 (cloning and expression of DNA coding for a glutathione S-transferase).

3. Genes that Confer or Contribute to a Value-Added Trait, Such as:

A) Modified fatty acid metabolism, for example, by transforming a plant with an antisense gene of stearyl-ACP desaturase to increase stearic acid content of the plant. See Knultzon et al. (1992) Proc. Natl. Acad. Sci. U.S.A. 89:2624.

B) Decreased phytate content. Introduction of a phytase-encoding gene may enhance breakdown of phytate, adding more free phosphate to the transformed plant. See, e.g., Van Hartingsveldt et al. (1993) Gene 127:87 (nucleotide sequence of an *Aspergillus niger* phytase gene). A gene may be introduced to reduce phytate content. In maize for example, this may be accomplished by cloning and then reintroducing DNA associated with the single allele which may be responsible for maize mutants characterized by low levels of phytic acid. See Raboy et al. (1990) Maydica 35:383.

C) Modified carbohydrate composition effected, for example, by transforming plants with a gene coding for an enzyme that alters the branching pattern of starch. See, e.g., Shiroza et al. (1988) J. Bacteol. 170:810 (nucleotide sequence of *Streptococcus* mutant fructosyltransferase gene); Steinmetz et al. (1985) Mol. Gen. Genet. 20:220 (levansucrase gene); Pen et al. (1992) Bio/Technology 10:292 (α-amylase); Elliot et al. (1993) Plant Molec. Biol. 21:515 (nucleotide sequences of tomato invertase genes); Sogaard et al. (1993) J. Biol. Chem. 268:22480 (barley α-amylase gene); and Fisher et al. (1993) Plant Physiol. 102:1045 (maize endosperm starch branching enzyme II).

C. Nanoparticles

According to some embodiments of the invention, methods are provided of introducing a linear nucleic acid molecule of interest into a cell comprising a cell wall (e.g., a plant cell). In some embodiments, the method may comprise placing a nanoparticle coated with a linear nucleic acid molecule of interest in contact with the cell, and allowing uptake of the nanoparticle across the cell wall. In particular embodiments, the nanoparticle may be reversibly or irreversibly contain, be coated with, or otherwise be bound to and/or carry a linear nucleic acid molecule of interest. In certain embodiments, a linear nucleic acid molecule of interest may be introduced to the nanoparticles before contact with a plant cell having a cell wall, or concurrently with the introduction of the nanoparticle to a plant cell having a cell wall. Examples of nanoparticles that can be used in embodiments of the present invention include without limitation quantum dots, either alone or in combination with semiconductor nanoparticles; positively-charged nanoparticles; gold nanoparticles; gold coated nanoparticles; porous nanoparticles; mesoporous nanoparticles; silica nanoparticles; polymer nanoparticles, including dendrimers; tungsten nanoparticles; gelatin nanoparticles; nanoshells; nanocores; nanospheres; nanorods; and magnetic nanoparticles.

According to embodiments of the present invention, a plant cell having a cell wall may be any plant cell comprising an intact and whole cell wall. Examples of plant cells having a cell wall include without limitation: algal; tobacco; carrot; maize; canola; rapeseed; cotton; palm; peanut; soybean; sugarcane; *Oryza* sp.; *Arabidopsis* sp.; and *Ricinus* sp. Embodiments of the invention may include cells comprising a cell wall from any tissue or wherever they are found, including without limitation: in embryos; meristematic cells; callus; pollen, including haploid and double haploid microspores; leaves; anthers; roots; root tips; flowers; seeds; pods; stems; and tissue culture.

In embodiments of the invention, a linear nucleic acid molecule of interest may be any nucleic acid molecule that can be delivered to a plant cell having a cell wall according to the present invention. Nucleic acid molecules of interest may comprise without limitation: DNA; RNA; RNAi molecules; genes; plasmids; cosmids; YACs; and BACs. Nucleic acid molecules of interest may be introduced to a plant cell having a cell wall concurrently with, for example and without limitation: polypeptides; enzymes; hormones; glyco-peptides; sugars; fats; signaling peptides; antibodies; vitamins; messengers; second messengers; amino acids; cAMP; drugs; herbicides; fungicides; antibiotics; and/or combinations thereof.

In particular embodiments of the invention, the surface of the nanoparticle may be functionalized, which may, for example, allow for targeted uptake or allow for reversible or irreversible binding of other substances to the surface of the nanoparticle. By way of non-limiting example, the surface of a nanoparticle (e.g., quantum dots) might be functionalized with a self-assembled monolayer of, for example, alkanethiolates, which can be further functionalized or derivatized. In a further non-limiting example, the surface of a nanoparticle may be derivatized with linkers which themselves may be further functionalized or derivatized. In one embodiment, a nanoparticle may be PEGylated. In other embodiments, the nanoparticle may comprise, or may be multifunctionalized with, one or more of a core (active or inactive); a steric coat (active or inert); a cleavable linkage; and/or a targeting molecule or ligand.

Nanoparticles such as quantum dots may be functionalized with PEG using the protocol of Dubertret et al. (2002) Science 298:1759, or by a protocol modified therefrom according to the discretion of the skilled artisan. For example, TOPO (tri-octyl phosphine oxide)-coated CdSe/ZnS quantum dots may suspended with PEG-PE in chloroform, followed by evaporation of the solvent and solubilization of the resulting PEGylated quantum dots with water.

In aspects of the invention, the nanoparticle may be taken up into various parts of cells. Examples of locations that a nanoparticle may be taken up into include without limitation: the cytosol; the nucleus; tonoplasts; plastids; etioplasts; chromoplasts; leucoplasts; elaioplasts; proteinoplasts; amyloplasts; chloroplasts; and the lumen of a double membrane. In other embodiments, nanoparticle uptake into a cell comprising a cell wall may occur via the symplastic or apoplastic pathway.

D. Stably Transformed Plant Cells

A stably-transformed plant cell according to the invention may be any plant cell capable of being transformed with a linear nucleic acid molecule of interest by nanoparticle-mediated transformation. Accordingly, the plant cell may be isolated from or cultured from a dicot or monocot. The plant cell may also be present in plant tissue or a whole plant. Non-limiting examples of stably transformed plant cells from dicotyledonous plants according to the invention include: alfalfa; beans; broccoli; cabbage; carrot; cauliflower; celery; Chinese cabbage; cotton; cucumber; eggplant; lettuce; melon; pea; pepper; peanut; potato; pumpkin; radish; rapeseed; spinach; soybean; squash; sugarbeet; sunflower; tobacco; tomato; and watermelon. Non-limiting examples of stably transformed plant cells from monocotyledonous plants according to the invention include corn; onion; rice; sorghum; wheat; rye; millet; sugarcane; oat; triticale; switchgrass; and turfgrass.

Transgenic plants according to the invention may be regenerated from stably transformed plant cells produced by methods of the invention. Such plants may be used or cultivated in any manner, wherein presence of the nucleic acid molecules of interest is desirable. Accordingly, transgenic plants may be engineered to, inter alia, have one or more desired traits, by being transformed with linear nucleic acid molecules via nanoparticle-mediated transformation, and cropped and cultivated by any method known to those of skill in the art.

The following examples are provided to illustrate certain particular features and/or embodiments. The examples should not be construed to limit the invention to the particular features or embodiments exemplified.

EXAMPLES

Example 1

Preparation of Nanoparticles for Plant Cell Transformation

Preparation of Plasmid DNA pDAB3831 plasmid DNA, FIG. 1, was isolated and prepared for Linear-DNA/PEGylated Quantum Dot (PQD)-mediated plant transformation. This plasmid contains the PAT selectable marker gene driven by the *Arabidopsis* Ubiquitin 10 promoter (AtUbi10) and the *Philadium* Yellow Fluorescence Protein gene (PhiYFP) driven by the Cassava Vein Mosaic Virus promoter (CsVMV). An *Escherichia coli* strain containing the plasmid was inoculated and grown to turbidity in Luria-Bertani broth containing ampicillin at 37° C. DNA was isolated using the QIAGEN® Plasmid Midi-Prep kit (Qiagen, Valencia, Calif.). Isolated DNA was linearized via a restriction enzyme digestion. The restriction enzyme, KpnI, was used to digest the DNA, thereby resulting in linearized plasmid DNA.

Formation of Linear DNA-PQD Complexes

Quantum Dots were obtained from Ocean Nanotechnology (Springdale, Ariz.). 2 mg of the TOPO (tri-octyl phosphine oxide)-coated CdSe/ZnS Quantum Dots were suspended with 0.15 gm (5.5 uMol) of PEG-PE (1,2-diacyl-sn-glycero-3-phosphoethanolamine-N-[methoxy-poly(ethylene glycol)]) (Avanti Polar Lipids, Alabaster, Ala.) in chloroform followed by evaporation of the solvent and solubilization with water. PEG conjugation was completed to protect against cytotoxicity.

The PQDs were conjugated to linear plasmid DNA. 2 mg of the PQDs were suspended with 4 mg of $HS-PEG-OCH_3$ (Prochimia, Zacisze, Poland) overnight at ~60-70° C. The solvent was removed in a vacuum oven. The residue was then suspended in 1 mL of water (18M). The last step is accompanied by a change of the red residue to an orange, optically clear, transparent solution. To coat linearized plasmid DNA onto $H_3CO$-PET-SH-QDs for transformation experiments, 0.02 mg of purified linearized plasmid DNA (pDAB3831) was incubated with the resultant PQD conjugate in 2 mL of water for 2 hours at 23° C. in the dark. Torney, et al. (2007) Nature Nanotechnol. 2:295-300.

Example 2

Transformation of *Arabidopsis* Floral Buds

For in planta genetic transformation, pDAB3831 plasmid was digested with KpnI restriction enzyme to linearize the DNA. After the restriction enzyme digestion, the linearized DNA was used in a specific ratio of PEG, QD, and linear DNA.

The linearized DNA was mixed with quantum dots, PEG, and incubated for 30 minutes. Then, the nanocomplex consisting of nanoparticles and linearized plasmid DNA solution was mixed with the working solution with 5% sucrose solution in water with 0.02-0.04% SILWET L-77®.

Plant Material for in Planta Transformation

Synchronized germination of the seed is important to ensure the uniformity of floral development in the $T_0$ plants. *A. thaliana* cv. Columbia seed was suspended in 0.1% (w/v) agar solution and incubated at 4° C. for 48 hours to complete stratification. 60 mg of seed was weighed and transferred to a 15 mL tube. 13 mL of 0.1% (w/v) agar solution was added and was vortexed until seed was evenly dispersed. This makes a seed solution concentration of 4.6 mg seed/1 mL of 0.1% (w/v) agar solution (or about 230 seeds/mL). 6 tubes (72 mL solution) were prepared to sow 4 flats that contain 18 (3½-inch) pots in each tray. The seed solution was incubated at 4° C. for 48 hours to complete stratification. Each pot was sown individually at 1.0 mL of stratified seed solution per pot. When all the pots were sown, propagation domes were placed on the trays to keep the soil moist. The domes were removed 5 days after the sow date. Seeds were germinated and plants were grown in a CONVIRON® (models CMP4030 and CMP3244, Controlled Environments Limited, Winnipeg, Manitoba, Canada) under long day conditions (16 hours light/8 hours dark) at a light intensity of 120-150 $\mu mol/m^2 sec$ under constant temperature (22° C.) and humidity (40-50%). Plants were watered 10 to 14 days after sowing the plants with Hoagland's solution and subsequently with DI water to keep the soil moist but not wet. After 4 weeks post-sow date, the flowers were cut back to produce a more even growth of secondary flowers. In the 5th week post-sowing, the plants were prepared for the transformation process.

In Planta Transformation

Linear-DNA/PQD-mediated transformation of *A. thaliana* cv. Columbia was completed using a modified protocol from Clough and Bent. Clough and Bent (1998) Plant J. 16:735-43. A 20 mL suspension was made with the linear DNA/PQD complex solution at a concentration of 0.5 mg of Linear-DNA and 4 nM of PQD and used for treatments of the *Arabidopsis* plants (mostly immature flower clusters with some fertilized siliques). Before dipping plants, SILWET L-77® to a concentration of 0.05% (w/v) (250 µL/500 mL)-0.005% was added to the Linear-DNA/PQD solution and mixed well. Above-ground parts of plant were dipped in Linear-DNA/PQD solution for 30 seconds, with gentle agitation. Treated plants were placed on their sides for 30 minutes in shade at 22-24° C. The plants were transferred to the CONVIRONS® under conditions as described above and allowed to grow to maturity and to collect seeds.

Selection trays (10.5"×21"×1" trays) were used to screen bulk harvest seed from $T_0$ plants, approximately 10,000 seeds on each tray. Two controls were used to ensure selection spraying was done correctly; Col-0 negative transformant control and Columbia Col-0 wild type spiked with homozygous seed for PAT (phosphinothricin acetyl transferase) selectable marker as a positive transformant control. To achieve synchronization, seeds were stratified in a 0.1% (w/v) agar solution for 48 hours prior to sowing. To provide 10,000 seeds per selection tray, 200 mg of seeds were added to a 0.1% (w/v) agar solution and vortexed until the seeds were evenly suspended. The stratified seeds were then sowed on selection trays filled with Sunshine mix LP5 and sub-irrigated with Hoagland's solution. For the selection spray to be effective, it is important that the 40 mL of suspended seed is sown evenly onto the selection tray. After sowing, propagation domes were placed on each selection tray and plants were grown for selection. Propagation domes were removed approximately 5 days post-sowing.

Example 3

Analysis of Transformed *Arabidopsis*

Selection of Transformed Plants

Freshly harvested $T_1$ seed was allowed to dry for 7 days at room temperature. $T_1$ seed was sown in 26.5×51-cm germination trays, each receiving a 200 mg aliquot of stratified $T_1$ seed (~10,000 seed) that had previously been suspended in 40 mL of 0.1% (w/v) agarose solution and stored at 4° C. for 2 days to complete dormancy requirements and ensure synchronous seed germination.

Sunshine Mix LP5 was covered with fine vermiculite and subirrigated with Hoagland's solution until wet, then allowed to gravity drain. Each 40 mL aliquot of stratified seed was sown evenly onto the vermiculite with a pipette and covered with humidity domes for 4-5 days. Domes were removed 1 day prior to initial transformant selection using glufosinate postemergence spray.

Seven days after planting (DAP) $T_1$ plants (cotyledon and 2-4-1f stage, respectively) were sprayed five times consecutively within five days with a 0.2% (w/v) solution of LIBERTY® herbicide (200 g ae/L glufosinate, Bayer Crop Sciences, Kansas City, Mo.) at a spray volume of 10 mL/tray (703 L/ha) using a DeVilbiss compressed air spray tip to deliver an effective rate of 280 g ae/ha glufosinate per application. Survivors (plants actively growing) were identified 4-7 days after the final spraying and transplanted individually into 3-inch pots prepared with potting media (Metro Mix 360). Transplanted plants were covered with humidity domes for 3-4 days and placed in a 22° C. growth chamber as before or moved to directly to the greenhouse. Domes were subsequently removed and plants reared in the greenhouse (22±5° C., 50±30% RH, 14 h light:10 dark, minimum 500 $\mu E/m^2 s^1$ natural+supplemental light).

Molecular and Biochemical Analyses

Molecular analyses were carried out for PAT and YFP integration into the plant genome. The PCR amplification products were sequenced and compared with the transgene sequences.

Molecular analysis and evidence for the genomic integration of transgenes in the $T_1$ progeny of *Arabidopsis thaliana* (cv Columbia)

Genomic DNA from *A. thaliana* transgenic plants was extracted from leaf material of 6-week-old plants using Plant DNAZOL™ (Invitrogen) according to the manufacturer's instructions. PCR primers were designed for detection of the YFP and PAT transgenes. The YFP primers are presented as SEQ ID NO:1 and SEQ ID NO:2. The PAT primers are presented as SEQ ID NO:3 and SEQ ID NO:4.

gDNA PCR Amplification of Transgenes

PCR amplification reactions for PAT and YFP were completed using the TaKaRa EX TAQ™ kit (Takara, Otsu, Shiga, Japan). Gene products were amplified in a total reaction volume of 50 µL. The PCR reaction contained 100 ng genomic DNA template, 1× EX TAQ™ reaction buffer, 0.2 mM dNTP, 10 pMol of each primer, and 0.025 units/µL ExTaq. The following PCR conditions were used: 1 cycle at 96° C. for 5 min, and 31 cycles of the following conditions 94° C. for 15 sec., 65° C. for 30 sec, 72° C. for 1 min and a final extension of 72° C. for 7 min. PCR amplification product was analyzed by 0.8% TAE agarose gel electrophoresis and visualized by ethidium bromide staining. The DNA fragments were purified from the agarose gel using the QIAEX™ II gel purification kit (Qiagen, Valencia, Calif.).

The PCR fragments were sequenced using the PAT forward primer (SEQ ID NO: 3) and YFP forward primer (SEQ ID NO: 1) using advanced Sanger sequencing technology (MWG Biotech, Huntsville, Ala.). The sequence data was analyzed using Sequencher software.

The sequencing results of the PAT and YFP PCR amplicons matched the expected nucleotide sequence for these genes. These results clearly indicate that the PAT and YFP sequences from pDAB3831 were stably integrated into the gDNA of *Arabidopsis* using the PEGylated Quantum Dot and Linear-DNA transformation protocol.

Figure 2:
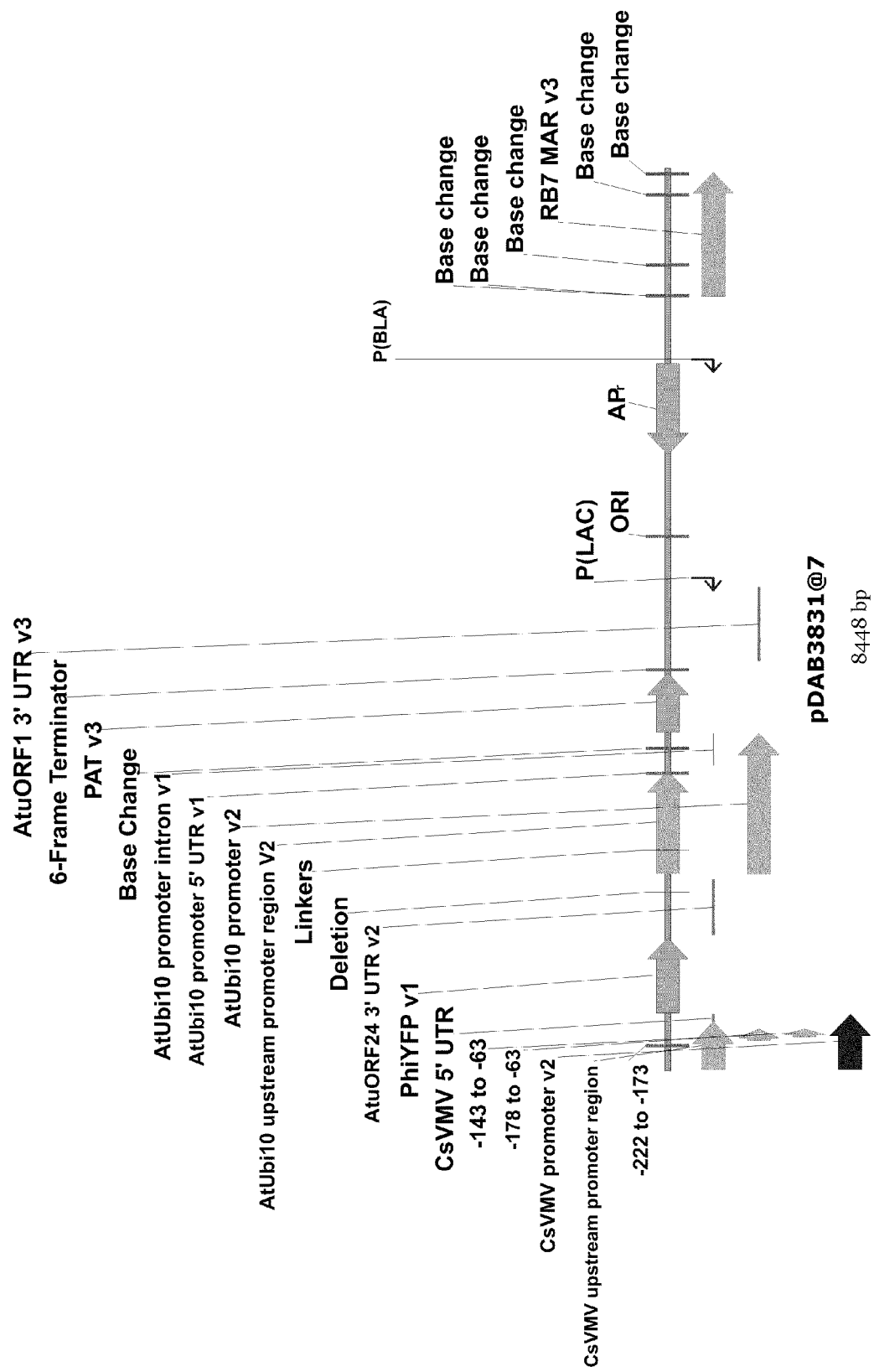
FIG. 2 includes a diagram of plasmid pDAB3831 linearized with KpnI restriction enzyme.

The PCR for PAT and YFP (Yellow Fluorescent tag, Evrogen) gene products were amplified in total reaction volume of 50 µL of the mixture containing 100 ng genomic template DNA, 1× EX TAQ™ reaction buffer (TaKaRa Bio), 0.2 mM dNTP, 10 µmol primer, and 0.025 units/µL ExTaq. The following PCR conditions were used: 1 cycle at 96 C for 5 min. and 31 cycles of the following PCR program: 94° C., 15 sec.; 65° C., 30 sec.; 72° C., 1 min. Final extension was performed at 72° C. for 7 minutes to complete PCR product synthesis. Gel images were obtained using BioRad Gel Imagining System. FIGS. 1 and 2. The amplified fragments were gel-purified using a gel purification kit (Qiagen Inc.) according to the manufacturer's instructions.

The PCR fragments were sequenced using PAT forward primer and YFP forward primer using advanced Sanger sequencing technology (MWG Biotechnologies, Inc.), and the sequence was analyzed using Sequencher software (Gene Codes Corp., Ann Arbor, Mich.).

The present results clearly indicates that the PAT and YFP sequences delivered through positively charged nanoparticle-mediated linearized DNA delivery in Example 1 and thus providing an evidence of stable genomic integration of transgenes in the genomic DNA of the $T_1$ plants of *Arapidopsis*.

Example 4

Nanoparticle-Mediated Delivery of Linear Nucleic Acid Molecules to Cultured Plant Cells Single Cell Plant Material is Prepared.

For example, both BY2 cells and NT1 cells are used. BY2 cells are a non-green, fast growing tobacco cell line. NT1 cells are photoautotrophic cells isolated from tobacco. Three to four days prior to transformation, a one-week-old suspension culture is subcultured to fresh medium by transfer of 2 ml of NT1 or BY2 culture into 40 ml NT1B or LSBY2 media containing 50 nM DAS-PMTI-1 (a microtubule inhibitor) and 0.5-0.1% (v/v) DMSO in a 250-mL flask. Single cells are collected either at four days or seven days after the microtubule inhibitor treatment. The BY2 single cells used are processed through a Beckman Flow cytometer to count the viable cells. The cells are examined using a Differential Interference Contrast (DIC) microscope attached to a confocal imaging system to determine that single cells comprise large numbers of plastids (amyloplasts) distributed throughout the cytoplasm of the cell. Cells are sub-cultured once in every 14 days by transferring 1 mL of suspension at 3.0 $OD_{600}$. Cultured cells are used as target cells for transformation.

Nanoparticle Preparation and Treatment of Cells

Plasmid DNA is isolated and prepared for Linear-DNA/PEGylated Quantum Dot (PQD)-mediated plant transformation. The plasmid contains the PAT selectable marker gene driven by the *Arabidopsis* Ubiquitin 10 promoter (AtUbi10) and the *Philadium* Yellow Fluorescence Protein gene (PhiYFP) driven by the Cassava Vein Mosaic Virus promoter (CsVMV). An *Escherichia coli* strain containing the plasmid is inoculated and grown to turbidity in Luria-Bertani broth containing ampicillin at 37° C. DNA is isolated using the QIAGEN® Plasmid Midi-Prep kit (Qiagen, Valencia, Calif.). Isolated DNA is linearized via a restriction enzyme digestion. The restriction enzyme, KpnI, is used to digest the DNA, thereby resulting in linearized plasmid DNA.

Quantum Dots are obtained from Ocean Nanotechnology (Springdale, Ariz.). 2 mg of the TOPO (tri-octyl phosphine oxide)-coated CdSe/ZnS Quantum Dots are suspended with 0.15 gm (5.5 uMol) of PEG-PE (1,2-diacyl-sn-glycero-3-phosphoethanolamine-N-[methoxy-poly(ethylene glycol)])

(Avanti Polar Lipids, Alabaster, Ala.) in chloroform, followed by evaporation of the solvent and solubilization with water. PEG conjugation is completed to protect against cytotoxicity.

The PQDs are conjugated to linear plasmid DNA. 2 mg of the PQDs are suspended with 4 mg of HS-PEG-OCH$_3$ (Prochimia, Zacisze, Poland) overnight at ~60-70° C. The solvent is removed in a vacuum oven. The residue is then suspended in 1 mL of water (18M). The last step is accompanied by a change of the red residue to an orange, optically clear, transparent solution. To coat linearized plasmid DNA onto H$_3$CO-PET-SH-QDs for transformation experiments, 0.02 mg of purified linearized plasmid DNA (pDAB3831) is incubated with the resultant PQD conjugate in 2 mL of water for 2 hours at 23° C. in the dark. Torney, et al. (2007) Nature Nanotechnol. 2:295-300.

A concentration of 1-3 μL/mL PQDs are added to 500 μL of cells in a 24-well micro titer plate and rotated on a shaker gently for 20 minutes in the dark. The nanoparticles are transported across the cell walls.

Example 5

Multifunctionalized Nanoparticle-Mediated in Planta Transformation of *Arabidopsis*

In planta transformation for *Arabidopsis* can be performed using a modified from Clough and Bent, 1998. Concentration of DNA on the multifunctionalized nanoparticle along with the molecules of homing protein transduction domain (PTDs) and NLS units are optimized to achieve increased transformation efficiency.

Plant material: Healthy *Arabidopsis* plants are grown under long days in pots in soil until flowering. First bolts are clipped to encourage proliferation of many secondary bolts. Plants are ready roughly 4-6 days after clipping. *Arabidopsis thaliana* Columbia (Col-0) ecotype is selected as the background (T$_0$ plant) for floral in planta transformation. Synchronized germination of the seed is important to ensure the uniformity of floral development in the T$_0$ plants. Wild Type seed is suspended in 0.1% agar solution and is incubated at 4° C. for 48 hours to complete stratification. 60 mg of seed is weighed on weigh paper and transferred to a 15 mL tube. 13 mL of 0.1% agar solution is added and vortexed until seed is evenly dispersed. This makes a concentration of 4.6 mg seed/1 mL solution (or about 230 seeds/mL). 6 tubes (72 mL solution) are prepared to sow 4 flats that contain 18 (3½-inch) pots in each tray and 2 total pots are sowed. The solution is incubated at 4° C. for 48 hours to complete stratification. Each pot is sown individually at 1.0 mL of stratified seed solution per pot. When all the pots are sown, propagation domes are placed on the trays to keep the soil moist. The domes are removed five days after the sow date. Seeds are germinated and plants are grown in a CONVIRON® (models CMP4030 and CMP3244, Controlled Environments Limited, Winnipeg, Manitoba, Canada) under long day conditions (16 hours light/8 hours dark) at a light intensity of 120-150 μmol/m$^2$sec under constant temperature (22° C.) and humidity (40-50%). Plants are watered 10 to 14 days after sowing the plants with Hoagland's solution and subsequently with DI water to keep the soil moist but not wet. After 4 weeks post-sow date, the flowers are cut back to produce a more even growth of secondary flowers. In the 5th week post-sowing, the plants are prepared for the transformation process.

Nanoconjugate preparation for floral treatments: Nanoparticles/quantum dots of 2-120 nm size ranges are chosen for treatments and are multifunctionalized with fragment purified pDAB3138 and the homing peptide units according to Derufus et al. (2007). Quantum dots with emission maxima of 655 or 705 nm and modified with PEG and amino groups are obtained from Quantum Dot Corporation (ITK amino). QD concentrations are measured by optical absorbance at 595 nm, using extinction coefficients provided by the supplier. Cross-linkers used are sulfo-LC-SPDP (sulfosuccinimidyl 6-(3'[2-pyridyldithio]-propionamido)hexanoate) (Pierce) and sulfo-SMCC (sulfosuccinimidyl 4-(N-maleimidomethyl)cyclohexane-1-carboxylate) (Sigma). Amino-modified QDs are conjugated to thiol-containing plasmid DNA and homing peptides using sulfo-LC-SPDP and sulfo-SMCC cross-linkers. QDs are resuspended in 50 mM sodium phosphate, 150 mM sodium chloride, pH 7.2, using AMICON® Ultra-4 (100 kDa cutoff) filters. Cross-linker (1000-fold excess) is added to QDs and allowed to react for 1 h. Samples are filtered on a NAP-5 gravity column (to remove excess cross-linker) into similar buffer supplemented with 10 mM EDTA. Linearized plasmid DNA, pDAB 3831 is treated with 0.1 M DTT for 1 h and filtered on a NAP-5 column into EDTA-containing buffer. Peptides are typically used from lyophilized powder. Peptide and linearized plasmid DNA are added to filtered QDs and allowed to react overnight at 4° C. Using three AMICON® filters, product is filtered twice with Dulbecco's phosphate-buffered saline (PBS), twice with a high salt buffer (1.0 M sodium chloride, 100 mM sodium citrate, pH 7.2), and twice again with PBS. High salt washes are required to remove electrostatically bound DNA and peptide, which is not removed with PBS washes alone. Sulfo-SMCC has an N-hydroxysuccinimide (NHS) ester at one end, which reacts with amino modified QDs to form an amide bond and a maleimide group at the other, which reacts with a thiolated plasmid DNA to form a thioether. Sulfo-LC-SPDP also contains an amine-reactive N-hydroxysuccinimide (NHS) ester which reacts rapidly with any primary amine-containing molecule thereby forming a stable amide bond.

In planta transformation and screening T$_1$ resistant plants: A final volume of 250-500 mL suspension is made with the nanoparticle, homing peptide and plasmid DNA (NHpD) conjugate solution and then the *Arabidopsis* plants (mostly immature flower clusters with some fertilized siliques) are used for treatments. Before dipping plants, SILWET L-77® to a concentration of 0.05% (250 ul/500 ml)-0.005% is added to the NHpD conjugate solution and mixed well. Above-ground parts of plant are dipped in NHpD conjugate solution for 2 to 30 seconds, with gentle agitation. Treated plants are kept under a dome or cover for 16 to 24 hours at 22-24° C. The plants are transferred to the CONVIRONS® and allowed to grow to maturity and to collect seeds. Selection trays (10.5"× 21"×1" trays) are used to screen bulk harvest seed from T$_0$ plants, approximately 10,000 seeds on each tray. Two controls are used to ensure selection spraying is done correctly, Col-0 negative transformant control and Columbia Col-0 wild type spiked with homozygous seed for PAT (Phospinothricin acetyl transferase) selectable marker as a positive transformant control. To achieve synchronization, seeds are stratified in a 0.1% (w/v) agar solution for 48 hours prior to sowing. To provide 10,000 seeds per selection tray, 200 mg of seeds are added to a 0.1% (w/v) agar solution and vortexed until the seeds are evenly suspended. The stratified seeds are then sowed on selection trays filled with Sunshine mix LP5 and sub-irrigated with Hoagland's solution. For the selection spray to be effective, it is important that the 40 mL of suspended seed is sown evenly onto the selection tray. After sowing, propagation domes are placed on each selection tray and the seeds are grown for selection using the conditions mentioned earlier. Propagation domes are removed approximately 5 days post-sowing. Seedlings are sprayed 5 days post-sowing and again 10 days post-sowing seedlings are sprayed with a 0.2% (v/v) solution (20 µl/10 ml dH2O) of glufosinate ammonium (LIBERTY® Herbicide from Bayer CropSciences) in a spray volume of 10 mL/tray (703 L/ha) using a DeVilbiss compressed air spray tip to deliver an effective rate of 280 g/ha glufosinate per application. The amount of LIBERTY® to prepare is calculated as follows: (703 L/ha spray volume=280 GPA). (280 g ai/ha)×(1 ha/703 L)×(1 L/200 g ai glufosinate)=0.20% solution (or 20 µL/10 mL). 10 mL of the solution is pipetted into a 20 mL scintillation vial for each tray to be sprayed. The spray is delivered using a horizontal and vertical application pattern. Four to seven days after the second spray herbicide resistant plants are identified.

What may be claimed is:

1. A method for introducing a linear nucleic acid molecule of interest into a plant cell having a cell wall, the method comprising:

providing the plant cell having a cell wall;

coating a semiconductor nanoparticle with polyethylene glycol;

coating the semiconductor nanoparticle with a linear nucleic acid molecule of interest;

placing the plant cell having a cell wall and the coated semiconductor nanoparticle in contact with each other;

allowing uptake of the semiconductor nanoparticle and the linear nucleic acid molecule of interest into the cell comprising a cell wall; by allowing translocation of the semiconductor nanoparticle and the linear nucleic acid molecule of interest across the cell wall and into the plant cell, wherein the translocation does not occur solely as a result of momentum imparted to the particle by something other than the cell into which the particle is being taken up; and selecting cells that have stably integrated the linear nucleic acid molecule of interest.

2. The method according to claim 1, further comprising allowing uptake of the nanoparticle into a compartment of the plant cell comprising a cell wall.

3. The method according to claim 2, further comprising coating the nanoparticle with a subcellular compartment targeting protein.

4. The method according to claim 3, wherein the compartment is selected from the group consisting of cytosol, nucleus, tonoplasts, plastid, etioplast, chromoplast, leucoplast, elaioplast, proteinoplast, amyloplast, chloroplast, and the lumen of the double membrane.

5. The method according to claim 1, wherein the plant cell having a cell wall is a plant cell from a commercial crop species.

6. The method according to claim 5, wherein the plant cell is selected from the group consisting of tobacco, carrot, maize, canola, rapeseed, cotton, palm, peanut, soybean, *Oryza* sp., *Arabidopsis* sp., *Ricinus* sp., and sugarcane cells.

7. The method according to claim 5, wherein the plant cell is from a tissue selected from the group consisting of embryo, meristematic, callus, pollen, leaves, anthers, roots, root tips, flowers, seeds, pods and stems.

8. The method according to claim 1, wherein the plant cell having a cell wall is a cultured cell.

9. The method according to claim 1, wherein the semiconductor nanoparticle is a quantum dot.

10. The method according to claim 1, wherein the linear nucleic acid molecule of interest comprises a nucleic acid sequence selected from the group consisting of DNA, RNA, RNAi molecules, and genes.

11. The method according to claim 10, wherein the linear nucleic acid molecule of interest comprises a gene.

12. The method according to claim 11, wherein the gene is a foreign protein gene, an agronomic gene, or a marker gene.

13. The method according to claim 1, wherein the linear nucleic acid molecule of interest is obtained from digestion of a nucleic acid molecule with a nuclease.

14. The method according to claim 13, wherein nucleic acid molecule digested with a nuclease is selected from the group consisting of plasmids, cosmids, artificial chromosomes, yeast artificial chromosomes, and bacterial artificial chromosomes.

15. The method according to claim 1, wherein the selected cells are regenerable cells.

16. The method according to claim 15, further comprising regenerating a plant from the regenerable cells.

17. A method for introducing a linear nucleic acid molecule of interest into plant material, the method comprising:
providing plant material comprising a plant cell having a cell wall, wherein the plant material is selected from the group consisting of plant cells, plant tissues, and plants;
coating a quantum dot nanoparticle with polyethylene glycol;
coating the quantum dot nanoparticle with a linear nucleic acid molecule of interest;
placing the plant material, comprising a plant cell having a cell wall, and the coated quantum dot nanoparticle in contact with each other;
allowing uptake of the quantum dot nanoparticle and the linear nucleic acid molecule of interest into cells of the plant material; by
allowing translocation of the quantum dot nanoparticle and the linear nucleic acid molecule of interest across the cell wall and into the plant cell, wherein the translocation does not occur solely as a result of momentum imparted to the particle by something other than the cell into which the particle is being taken up; and
selecting cells that have stably integrated the linear nucleic acid molecule of interest.

18. The method according to claim 17, wherein the plant material is plant tissue selected from the group consisting of embryo, meristematic tissue, callus, pollen, leaves, anthers, roots, root tips, flowers, seeds, pods and stems.

19. A method for introgressing a trait into a plant, the method comprising:
providing a plant cell;
coating a semiconductor nanoparticle with polyethylene glycol;
coating the polyethylene glycol coated semiconductor nanoparticle with a linear nucleic acid molecule of interest comprising a gene for expressing the trait in the plant;
placing the plant cell and the polyethylene glycol coated semiconductor nanoparticle, coated with the linear nucleic acid molecule of interest comprising the gene for expressing the trait in the plant, in contact with each other, so as to allow uptake of the semiconductor nanoparticle, and uptake of the linear nucleic acid molecule of interest comprising the gene for expressing the trait in the plant, into the plant cell; by
allowing translocation of the semiconductor nanoparticle and the linear nucleic acid molecule of interest across the cell wall and into the plant cell, wherein the translocation does not occur solely as a result of momentum imparted to the particle by something other than the cell into which the particle is being taken up, thereby transforming the plant cell;
regenerating a whole plant from the transformed plant cell; and
propagating the plant.

20. The method of claim 19, wherein the trait is selected from the group consisting of expression of a protein of interest, male sterility, herbicide resistance, insect resistance, resistance to bacterial disease, resistance to fungal disease, and resistance to viral disease.

21. A method for introducing a linear nucleic acid molecule of interest into a plant cell having a cell wall, the method comprising:
providing the plant cell having a cell wall;
coating a quantum dot nanoparticle with polyethylene glycol;
coating the quantum dot nanoparticle with a linear nucleic acid molecule of interest;
placing the plant cell having a cell wall and the coated quantum dot nanoparticle in contact with each other; and
allowing translocation of the quantum dot nanoparticle and the linear nucleic acid molecule of interest across the cell wall and into the plant cell, wherein the translocation does not occur solely as a result of momentum imparted to the particle by something other than the cell into which the particle is being taken up.

* * * * *